US005697920A

United States Patent [19]

Gibbons

[11] Patent Number: 5,697,920

[45] Date of Patent: Dec. 16, 1997

[54] BODY VACUUM

[76] Inventor: De Lamar Gibbons, 2592 McClelland St., Salt Lake City, Utah 84106

[21] Appl. No.: 587,892

[22] Filed: Jan. 16, 1996

Related U.S. Application Data

[63] Continuation-in-part of Ser. No. 942,060, Sep. 9, 1992, Pat. No. 5,484,427, which is a continuation-in-part of Ser. No. 642,996, Jan. 18, 1991, abandoned.

[51] Int. Cl.[6] .................. A61M 35/00

[52] U.S. Cl. .................. 604/289; 604/313

[58] Field of Search .................. 15/321–322, 346, 15/398; 604/289, 290, 313; 285/171

[56] References Cited

U.S. PATENT DOCUMENTS 1,821,715 9/1931 Kuchinsky .................. 15/321

2,177,987 10/1939 Kelly .................. 15/398

4,511,163 4/1985 Harris et al. .................. 285/177

*Primary Examiner*—Robert A. Clarke

*Attorney, Agent, or Firm*—Glenna Hendricks; Stephen Gates

[57] ABSTRACT

The invention requires a brush having a passage through which water forced under pressure is supplied to the brush area and having a passage attached to a vacuum. The water supply passage and the passage under vacuum must be so aligned that the cleaning solution is removed from the area to be cleaned along with debris without allowing the contaminated solution to collect on the surface of the skin. In the preferred embodiment of the invention, no moving parts are required for the brush. The brush may be made of any soft material that is easily cleaned. However, a brush made of soft plastic bristles such as those used for surgical scrub brushes is preferred. The invention does not require formation of a foam as a cleansing agent.

10 Claims, 5 Drawing Sheets

BODY VACUUM

This application is a continuation-in-part of U.S. Ser. No. 07/942,060 filed Sep. 9, 1992, now issued as U.S. Pat. No. 5,484,427, which is a continuation-in-part of U.S. Ser. No. 07/642,966 filed Jan. 18, 1991, now abandoned.

FIELD OF THE INVENTION

This invention is related to means for cleaning surfaces. The cleaning of objects using controlled exposure to the cleaning fluid is particularly desirable in many instances where either there is need to avoid exposure of the surrounding area to moisture or there is need to protect the environment, including care givers, from the used cleaning medium. Such instances include the washing of patients that must be confined to bed and trauma patients in surgery or emergency care facilities. Furthermore, it is frequently difficult to provide adequate cleansing without moistening the bedding. The problem is particularly acute when exposure to the solution used for cleansing may damage the patient or increase discomfort, as is the case with burn patients or patients in body casts.

BACKGROUND OF THE INVENTION

Problems related to protection of the environment include care of patients with infectious diseases or practice of cleaning processes that use harmful cleaning solutions or remove environmentally harmful substances from the area being cleansed. Patient bathing devices have been known. A few of these devices use a suction means for removing cleansing fluid and debris.

The use of portable scrubbing devices has been known. U.S. Pat. No. 3,574,239 to Sollerud discloses a portable bathing device for use in bathing patients in hospital and nursing home settings. The device is, however, limited in its application since it is housed in a rather large unit that must be wheeled to the bedside. Furthermore, the invention of Sollerud uses a sponge surrounded with a concentric passageway connected to a vacuum. The device requires a foaming cleaning solution under pressure to clean the wound, and would not be appropriate for removing bits of glass or other debris from wounds. Other scrubbing devices for use in cleaning of carpeting and hard surface floors have, of course, been known, but such devices are often unwieldy and are not adapted for meeting a wide range of cleaning applications. Most particularly, they are not adapted for use in cleaning skin or other surfaces requiring gentle, controlled cleaning.

U.S. Pat. No. 4,900,316 to Yamamoto discloses a suction device for use in cleaning and suctioning the skin. The device uses a suction cap. The device requires access to modern plumbing and is useful only for removing small amounts of undesirable matter from the skin.

DISCLOSURE OF THE INVENTION

The subject invention provides a means of cleaning body surfaces with a portable device that may be either connected to a vacuum or can be used as an adaptation to currently used cleaning machines. While the invention has been particularly adapted for use in cleaning the skin and its appendages, it is deemed useful for any application requiring gentle cleaning and removal of debris with maximum control of the cleansing solution and/or debris.

BRIEF DESCRIPTION OF THE DRAWINGS

FIG. 1 is a schematic view of the invention having a solution supply (1), a conduit carrying solution under pressure (2), a brush having soft bristles (3), and a conduit to a negative pressure source (4).

FIG. 2 is a schematic view of some preferred brushes used to clean patients wherein the bristles are of soft plastic. FIG. 2(*a*) shows the brush having a large conduit to the suction unit. FIG. 2(*b*) shows a unit particularly useful with standard plastic tubing. FIG. 2(*c*) shows an alternative brush arrangement. FIG. 2(*d*) shows a connector for use when no trap is required.

FIG. 3 is a schematic view of the invention adapted for the cleaning device disclosed in U.S. Pat. No. 4,803,466, which is incorporated herein by reference, namely, the Ultimate cleaning device available from U.S. Products, Inc. of Hayden Lake, Id. in the United States.

FIG. 4 is a schematic view wherein the fluid supply is a bag filled with sterile solution and wherein the pressure is provided by gravity and the negative pressure source is a wall suction. FIG. 5(*a*) shows a round brush portion. FIG. 5(*b*) shows an oval brush portion.

MODES FOR CARRYING OUT THE INVENTION

The subject invention provides a means for cleaning in instances where it is necessary to avoid exposure the area surrounding the area being cleaned to cleaning solution and debris. The invention is useful for purposes of protecting care deliverers from exposure to infectious organisms or toxic substances. The subject invention also provides a means of cleaning patients while protecting dressings from exposure to fluid used in cleaning.

Figure 1:
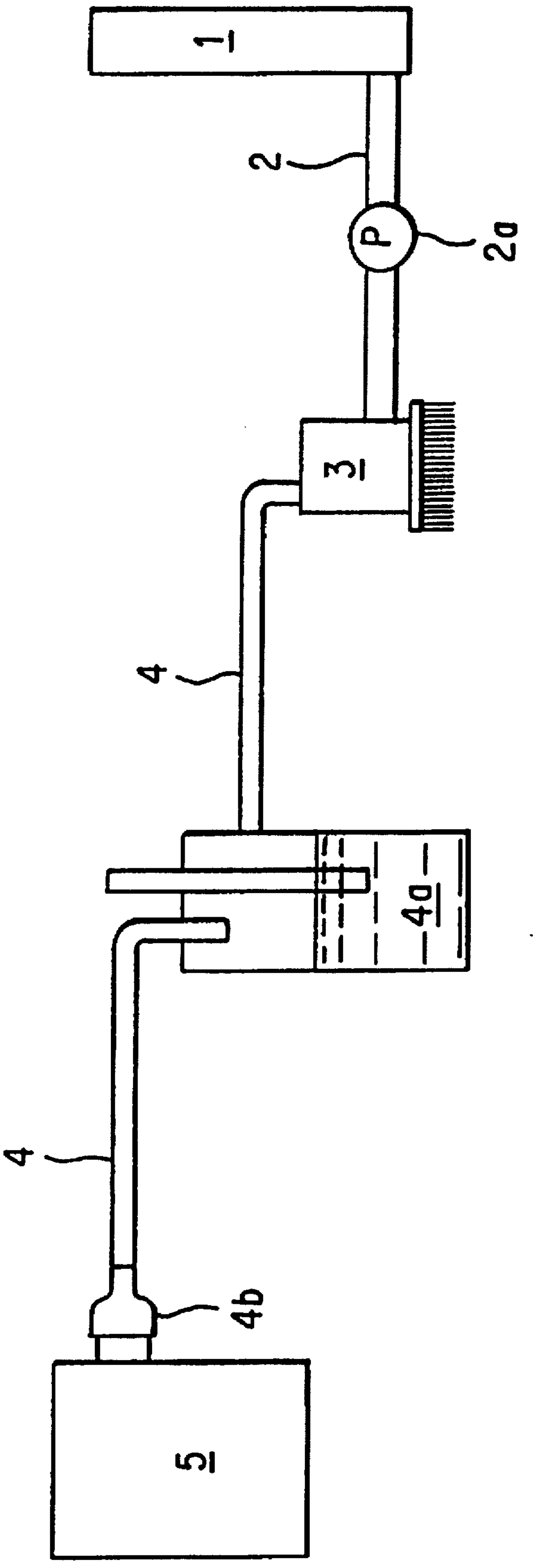
FIG. 1.

Referring now to the drawings, FIG. 1 is a schematic view of the invention. The system requires a source of solution (1). The solution source is not important and can be, for example, a tank in a cleaning device such as that disclosed in U.S. Pat. No. 4,803,466, a bag or bottle of sterile fluid hung on a standard, or a water faucet. A conduit (2) from the water supply carries the solution under pressure to the brush. The source of the pressure is not important. The pressure may result from the force of gravity as would result if a container of fluid were held above the level of the brush on a standard such as that usually used to administer intravenous feedings. Alternatively, the solution may be forced under pressure from a pump means (2*a*). The solution must enter the brush unit (3) near the bristles. The solution is then removed by lift provided from a negative pressure generator (5) through the conduit (4). The source of negative pressure generator may be a vacuum pump that is part of a cleaning machine, a wall suction in a care facility, or a household vacuum cleaner. If household vacuum cleaner is used, the conduit must be equipped with a trap (4*a*) for collecting the used solution and other debris. In the latter case, the part of the conduit leading from the trap must have, at its end, an adaptive connection for attachment to the vacuum cleaner as shown at 4*b* (insert). If the negative pressure generator is a wet/dry vacuum, a connector as shown in the 4*b* insert may be attached to the conduit from the brush portion without use of a trap.

Preferred embodiments of the brush unit adapted for attachment to the conduit from the solution supply source and a negative pressure generator are shown in FIG. 2. The brush portion (1) has conduits equipped with connectors (2) and (3) adapted for connection to the solution supply and suction units. FIG. 2(*a*) shows the brush having a large conduit to the suction unit. This arrangement was used successfully with the cleaning device disclosed in U.S. Pat. No. 4,803,466 known as Ultimate PB-III (hereinafter referred to as "Ultimate". FIG. 2(*b*) shows a unit particularly useful with standard plastic tubing connected to the suction apparatus with traps commonly used in hospitals, or for use with wall suction. FIG. 2(*c*) shows an alternative arrangement for the brush wherein the bristles are surrounded by a concentric passage under negative pressure. FIG. 2(*d*) shows a connector that may be used with a wet/dry vacuum when no trap is required.

Figure 2A:
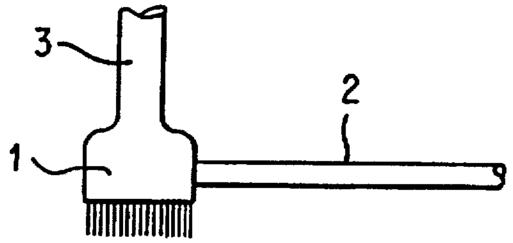
FIG. 2.
Figure 2B:
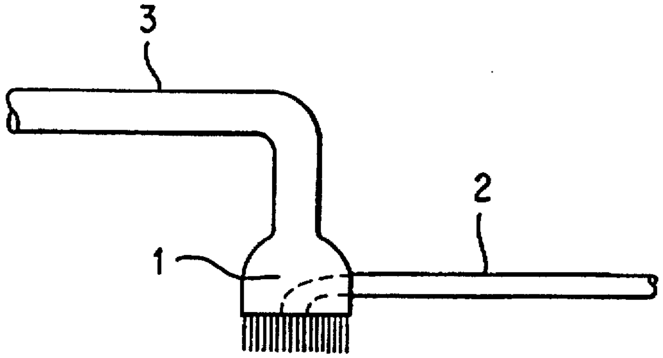
Figure 2C:
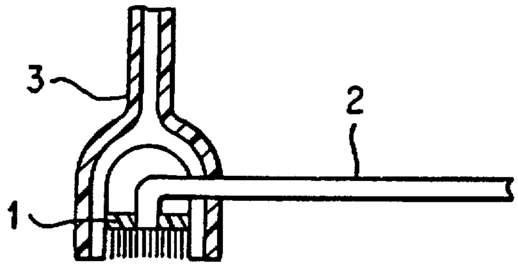
Figure 2D:
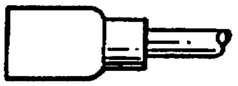
Figure 3:
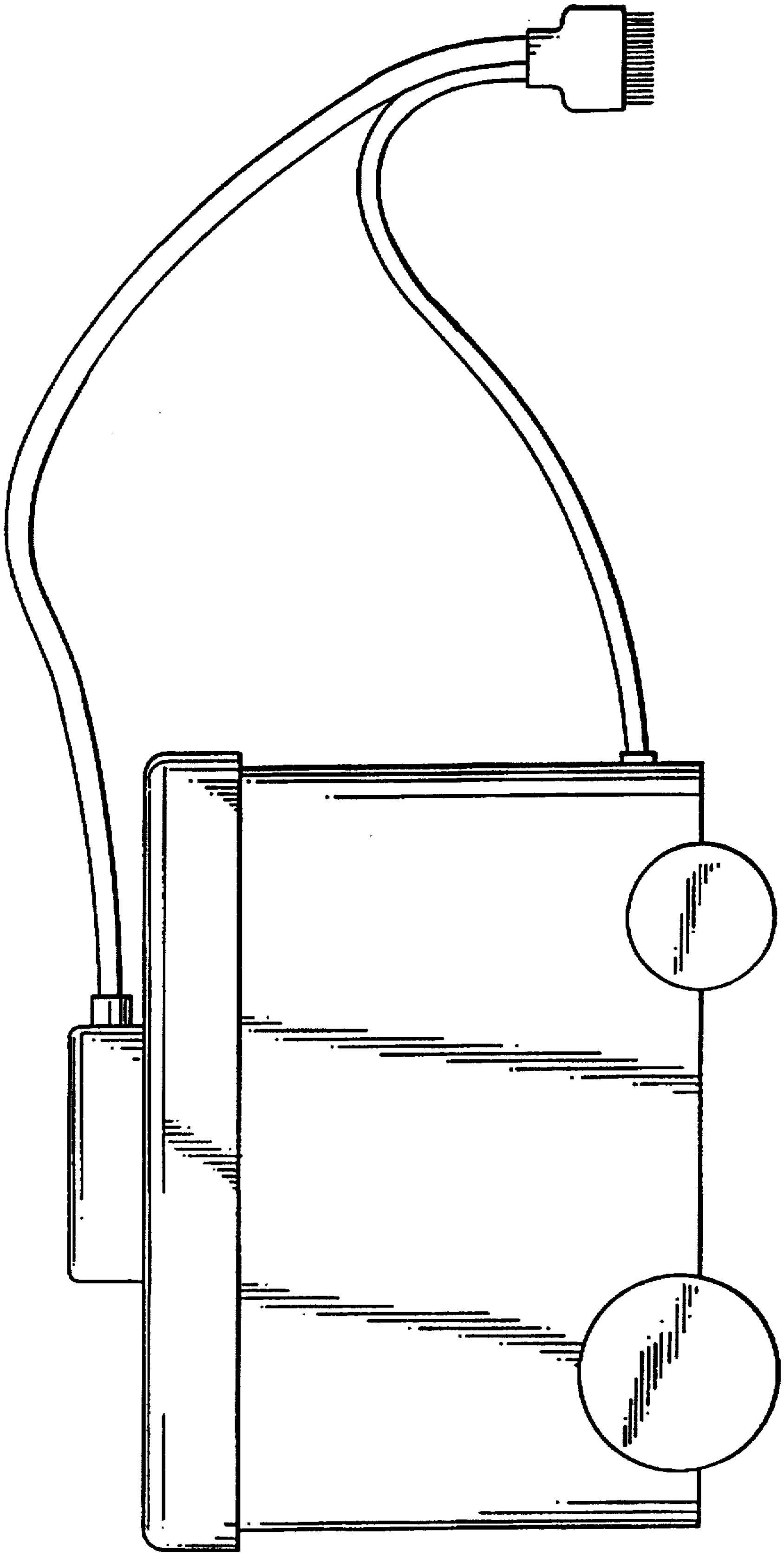
FIG. 3.

FIG. 3 depicts the brush arrangement of FIG. 2(*a*) as used with the "Ultimate" cleaner, which comes equipped with a unit that warms the solution and holds it at the desired temperature. The device as illustrated would be useful in nursing homes and other care facilities where there was a desire to clean many patients suffering from incontinence or infectious disease.

One important feature of the unique devices and methods of the invention for use in protecting care-givers from exposure to infection or toxic substances is the capability for treating used solution before it is discharged into the environment. In a preferred embodiment, the spent/soiled fluid can be retained in a trap for treatment with disinfectants or detoxifying means (whether chemical or physical) before appropriate disposal.

The invention can, of course, be used to clean any person, whether well or ill. When used for patient care, it is possible to wash the patient without exposing areas covered with bandaging or casts to the fluid. It is also possible to wash patients suffering burns without exposing the nearby burned areas to the cleansing fluid. The invention is very useful for cleaning victims of trauma who have debris such as glass imbedded in bruised areas of flesh. The use of the brush having soft bristles that will not mat in conjunction with the lift provided by the vacuum would remove the imbedded debris without adding to the trauma affecting the underlying tissues. The brush must have bristles that will spring back after displacement from rubbing, in other words, that will not mat, in order to be useful for this purpose, since it is necessary that the water flow not be obstructed and that the individual bristle tips be available to the surface being cleansed if maximum benefit is to be obtained when cleansing such wounds. The preferred length for the bristles is 0.3 to 1.5 inch.

Figure 4:
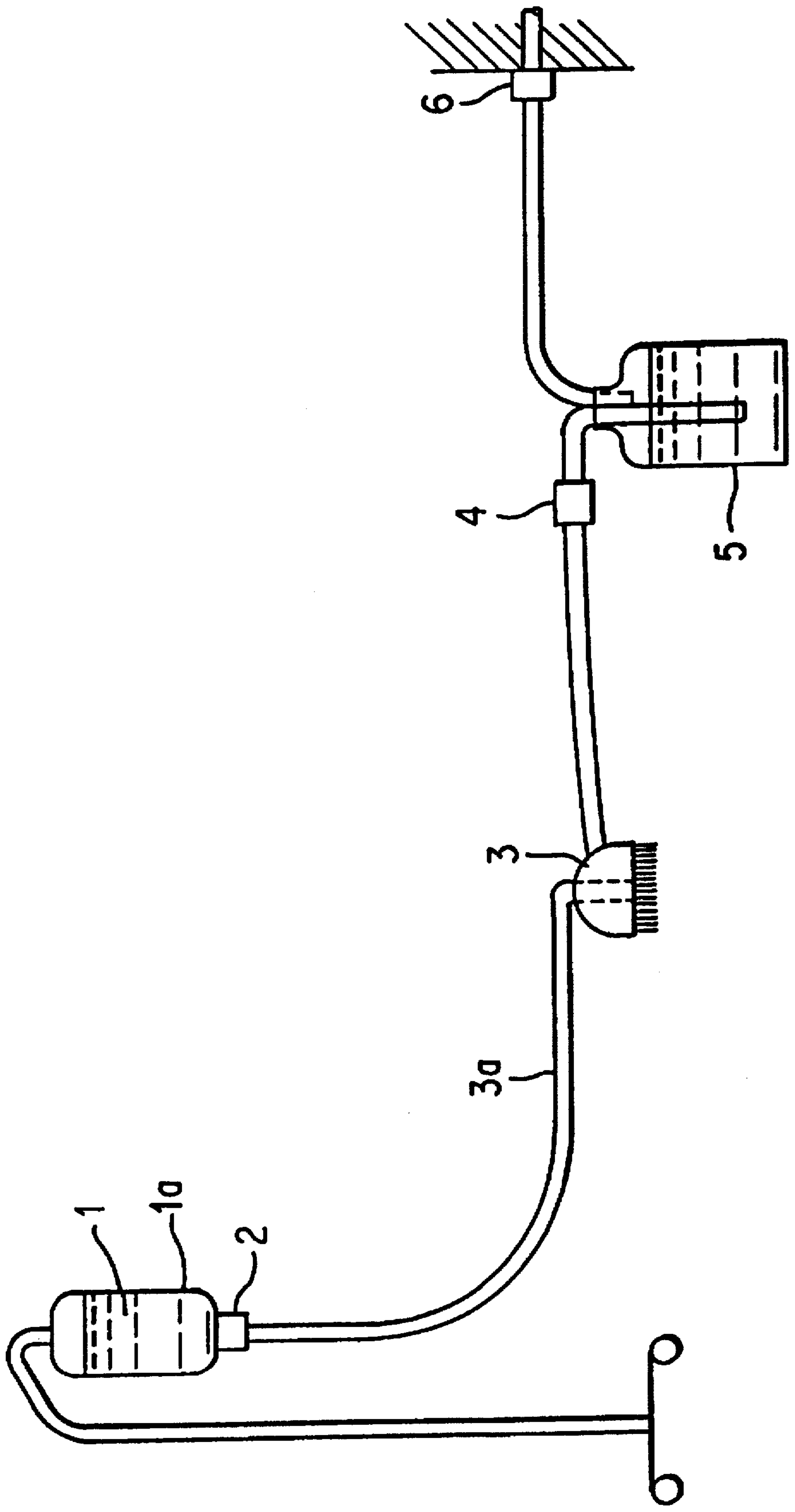
FIG. 4.

FIG. 4 provides a schematic drawing of the invention using as a negative pressure source a wall suction (5) such as that found in hospital and other care facilities. The source of solution (1) is a bag of fluid. The fluid can contain, for example, disinfectants and detergents. The brush unit (3) is attached through a tubular conduit (3*a*) to the conduit from the fluid bag (1*a*) through a connector (2). A preferred connector would comprise an integral extension which is a cylindrical screw having a graduated cylinder size with external threads that would be inserted into the conduit from the solution supply. It is appreciated that the screw arrangement will allow access of the connector to tubular conduits of varying sizes. The conduit from the brush to the vacuum is attached by a second connector (4) through a trap (5) to the wall suction (6). If controlled collection of the solution is not required, there is no need for a trap. In that instance the conduit from the brush may attach directly to the hollow cylindrical screw of the wall suction.

Figure 5A:
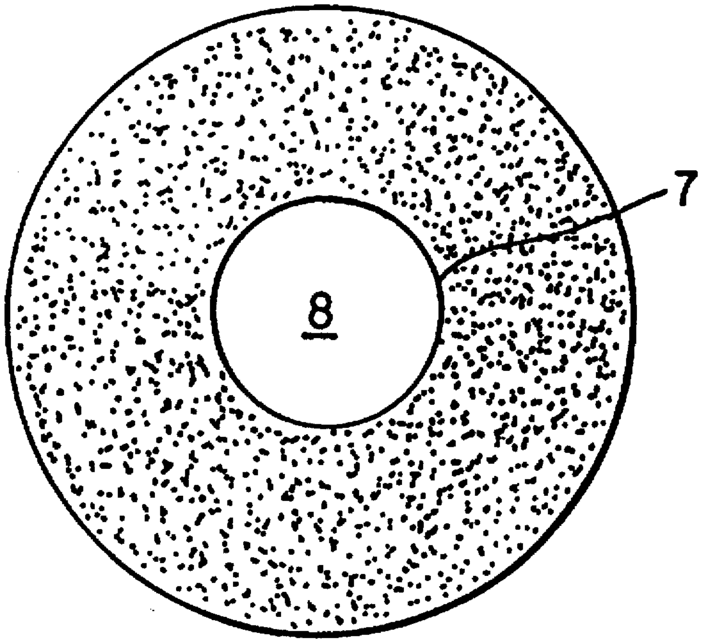
FIG. 5.
Figure 5B:
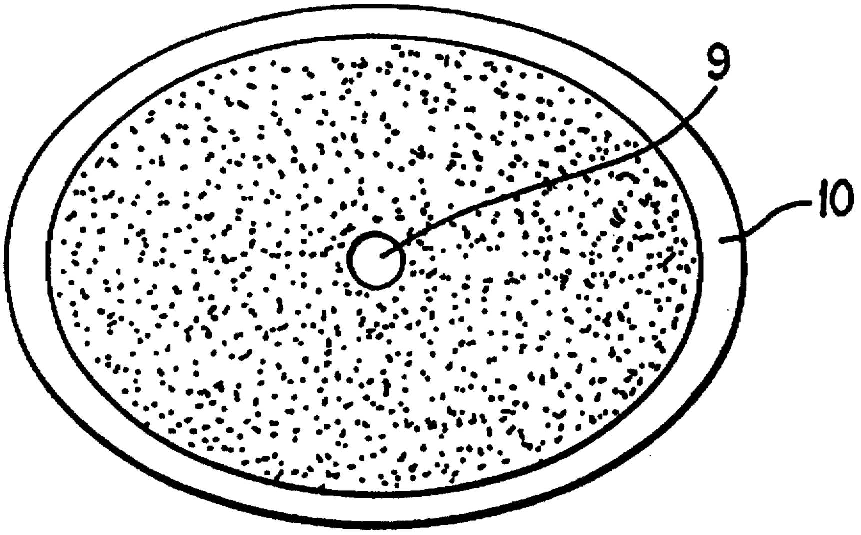

FIG. 5(*a*) shows a round brush having an inlet (7) near the base of the bristles and a opening (8) in the center of the brush through which the fluid is sucked by negative pressure. FIG. 5(*b*) shows an oval brush having an opening for inflow of fluid at (9) and a conduit (10) that encircles the bristles wherein the conduit encircles the bristles. Under operating conditions the water in the encircling conduit is under negative pressure.

It is possible to avoid contact in the general environment with the spent fluid, body discharges and fluids containing disease inducing contaminants, since the suction may be attached to the vacuum source through a trap that will contain substances that will render the used cleansing fluid harmless. Even if the negative pressure providing device has a solution receiving device, it may be necessary to pass the spent/soiled fluid through a trap before discharge into the solution-receiving area so that the solution can be treated. As an example, addition of chlorine or other disinfectants can be added to fluid in the trap before discharge into the environment. In some instances, it might be quite acceptable to simply pour the disinfectant into the discharge receptacle either before use of the device or after the soiled solution has been collected but before discharge into the environment.

The invention can be used to provide cleansing when there is a limited supply of water available, since the solution can be used more efficiently. Because the invention can be used with a wide variety of suction devices, it is necessary to transport only the fluid with scrubbing units to the user.

The invention is also useful for cleaning pets. It is particularly useful for cleansing in conjunction with use of pesticides such as flea repellents, since exposure of the care-taker to the pesticides is reduced.

If desired, the suction can be applied through a concentric passageway that surrounds the brush as illustrated in FIG. 2*c*. This arrangement may be particularly advantageous when it is crucial that no solution reach the surrounding area. Such control is particularly crucial in cleaning burn patients or patients in a cast. The concentric passageway design may also be particularly useful when it is desirable to use less lift, since the solution, if not contained by such a passage, is then more likely to escape the area being cleaned.

The brush may be any shape, though the round or oval shape is preferred for purposes of cleansing the skin.

The method and devices of the invention make it possible to administer a sterile solution under pressure to a wound area in such a manner that the area is cleaned by the pressurized solution and the gentle agitation of the brush bristles. While it is often desirable to have a pump to force the cleaning solution against the surface being cleaned, in many instances, it is possible for gravity to provide sufficient pressure to the liquid. In such instances, the cleansing solution can easily be supplied in bags or bottles. This arrangement provides a ready means of cleansing wounds of patients in surgical or emergency care units with sterile solution wherein the brush is attached though the connector to the bag of solution and the second connector is attached to a wall suction.

For purposes of daily cleaning of patients, a cleaning device such as The Ultimate cleaning device of U.S. Products, Inc. of Hayden Lake, Id. is appropriate. The brush unit could be stored at the beside of each patient and could then be connected to the unit as needed. However, since the unit having the connectors and the brush would be relatively inexpensive, the brush unit could be disposed of after each use. It would not be necessary for such a device to have a heat exchanger as shown with the product of U.S. Products for purposes of washing patients. It would be necessary to use the brush as modified in the present invention to provide the necessary gentle cleansing needed in patient care. The container for the soiled solution will entrap any deleterious components such as asbestos or harmful infectious organisms for safe disposal and/or disinfecting.

The brush unit with connectors as exemplified in FIG. 2 may be sold as a unit for patient care. The connector means may be attached to the conduits or provided separately. Alternatively, kits containing the brush portion and a container of appropriate cleansing fluid may be provided. Solution may contain, for example, antiseptics or pharmaceutically active agents such as astringents or steroids.

For veterinary uses, kits containing the brush unit and pesticidal solutions may be provided. The pesticidal agents may be provided as concentrates or dissolved solution ready for use.

All references cited in this document are incorporated herein by reference.

I claim:

1. A device adapted for cleaning the skin and its appendages comprising a brush portion having soft bristles of 0.3 to 1.5 inches in length that do not mat, said brush portion having two conduits attached thereto wherein the first conduit is equipped at the end distal to said brush with a connector adapted for connection to a solution supply source and at the end of said first conduit proximal to said brush portion delivers said solution directly into said brush portion at or immediately above said bristles, and wherein the second conduit leads from said brush, said second conduit leading to a negative pressure source, said second conduit having a first opening into said brush portion near the bristles of said brush portion, said second conduit having at the end distal from said brush portion a negative pressure generator.

2. A device of claim 1 wherein the fluid in said second conduit is discharged into a trap.

3. A device of claim 1 wherein the bristles are made of plastic.

4. A device of claim 1 wherein the connector of the first conduit distal to the brush portion is an integral extension of said conduit wherein said connector is a cylindrical screw having a graduated size with external threads adapted for insertion into a conduit from the solution supply.

5. A device of claim 1 wherein the negative pressure is applied through a concentric passageway that surrounds the brush.

6. A device according to claim 1 wherein said brush is round or oval.

7. A device according to claim 1 wherein said negative pressure source is a wall suction.

8. A device according to claim 1 wherein said connector between said second conduit and said brush portion is an integral extension of said conduit and wherein said connector is a cylindrical screw having a graduated size with external threads.

9. A device according to claim 1 wherein said first conduit is attached to a supply source containing a sterile solution.

10. A device according to claim 1 wherein said first conduit contains a solution containing an antiseptic.

* * * * *